United States Patent
Chaudhari et al.

[11] Patent Number: 6,069,253
[45] Date of Patent: May 30, 2000

[54] PROCESS FOR THE PREPARATION OF NEW TRANSITION METAL COMPLEXES

[75] Inventors: Raghunath V. Chaudhari; Jayasree Seayad; Seayad A. Majeed, all of Maharashtra, India

[73] Assignee: Council of Scientific and Industrial Research, New Delhi, India

[21] Appl. No.: 09/281,929

[22] Filed: Mar. 31, 1999

[30] Foreign Application Priority Data

Dec. 9, 1998 [IN] India ............... 3698/DEL/98

[51] Int. Cl.[7] ............... C07F 15/00; B01J 31/00
[52] U.S. Cl. ............... 546/2; 546/5; 546/7; 556/23; 502/162; 502/163
[58] Field of Search ............... 556/23; 546/2, 546/5, 7; 502/162, 166

[56] References Cited

U.S. PATENT DOCUMENTS 3,287,455  11/1966  Malkin et al. ............... 260/270

4,171,360  10/1979  Hill ............... 424/245

*Primary Examiner*—Porfirio Nazario-Gonzalez
*Attorney, Agent, or Firm*—Birch, Stewart, Kolasch & Birch, LLP

[57] ABSTRACT

The present invention relates to novel group VIII transition metal complexes represented by the formula (I) as:

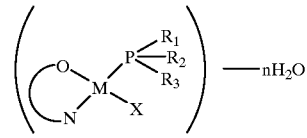

Formula 1 wherein M is the central transition metal; $N\frown O$ represents a semilabile anionic chelating ligand; $R_1$, $R_2$ & $R_3$ are substituents on the phosphine ligand, X is chosen from sulphonato, carboxylato, formato group or halides and $1<n<10$. The invention also provides a process for the preparation of said transition metal complex.

15 Claims, 1 Drawing Sheet

Formula 1

Formula 1

PROCESS FOR THE PREPARATION OF NEW TRANSITION METAL COMPLEXES

FIELD OF THE INVENTION

The invention relates to new transition metal complexes and a process for preparing the same. The complexes of the present invention are particularly useful as efficient catalysts for the carbonylation of olefins, dienes, alkynes, nitro compounds and alcohols and co-polymerization of olefins with carbon monoxide. More particularly, the invention relates to the preparation of a series of new group VIII metal complexes having the general formula 1 as shown in the accompanying drawings wherein M represents the central transition metal, N⌢O represents a semilabile anionic chelating ligand, and X is a sulphonato, carboxylato or formato group, or any of the halides and $R_1$, $R_2$ and $R_3$ are substituents of the phosphine ligand.

BACKGROUND OF THE INVENTION

Group VIII metal complexes containing bidentate ligands have been shown to be very effective catalysts for a variety of carbonylation and co-polymerization reactions. While a variety of complexes containing bidentate ligands are useful for such chemical conversions, the synthesis of stable metal complexes having high catalytic activity for a wide range of such reaction is often difficult.

Although many group VIII metal complexes involving bidentate ligands have been reported in the literature, the complex having the formula 1 has been synthesized for the first time and there is no prior art available for synthesizing these complexes.

OBJECTS OF THE INVENTION

The main object of the present invention is to provide novel transition metal complexes and a process for the preparation of a said class of group VIII metal complexes that may be useful as catalysts for carbonylation and copolymerization of a wide range of organic compounds.

BRIEF DESCRIPTION OF THE ACCOMPANYING DRAWINGS

FIG. 1 represents the formula of the transition metal complex of the invention.

DETAILED DESCRIPTION OF THE INVENTION

Figure 1:
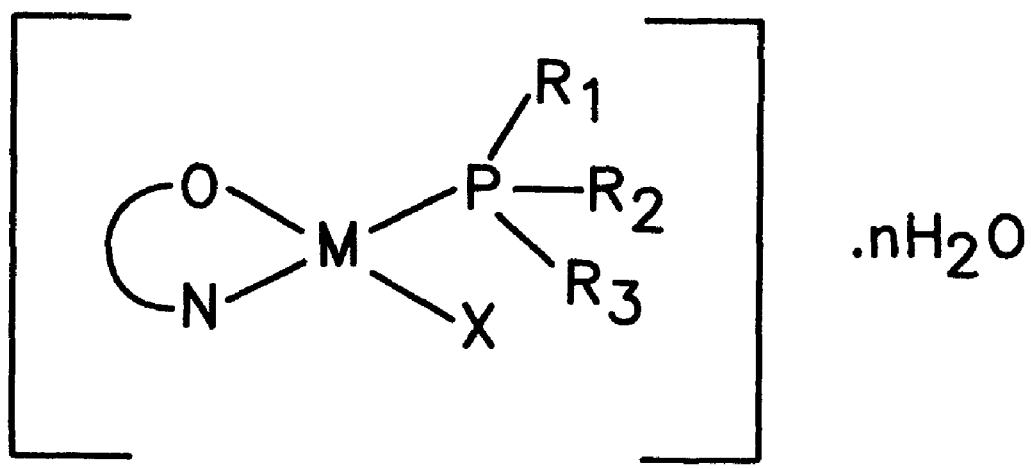

The invention relates to a novel class of group VIII stable transition metal complexes, especially those of palladium or platinum, involving semi labile, bifunctional ligands such as pyridine carboxylato as well as semi-labile ligands such as sulphonato, formato or carboxylato or halo groups are synthesized for the first time. The lability and bifunctional nature or the ligands provides good catalytic properties. The stability of the complexes makes handling and storage easy.

Accordingly, the present invention provides for a novel class of group VIII metal complexes having the general formula 1 as shown herein below and in the accompanying drawings wherein M is a group VIII transition metal; $R_1$, $R_2$, $R_3$=substituents on phosphine ligands, such as hydrogen, alkyl, arylalkyl, cycloaliphatic groups, X=aryl or alkyl sulphonato or aryl alkyl carboxylato or formato group or halides such as $Cl^-$, $Br^-$ or $I^-$ and $1<n<10$.

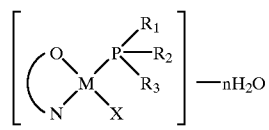

Formula 1

In another embodiment, the semilabile anionic chelating ligand in the compound having formula 1 may be an organic compound, containing a N doner and an $O^-$ group, exemplified by 8-hydroxy quinoline, 2-hydroxy pyridine, 2(-2 hydroxy ethyl) pyridine, pyridyl-2-carboxylate, quinolyl-2-carboxylate, isoquinolyl-1-carboxylate and isoquinolyl-3-carboxylate, particularly pyridyl-2-carboxylate, piperidyl-2 carboxylate, and 8-hydroxyquinoline.

In another embodiment, the group VIII metal source may preferably be palladium or platinum compounds such as palladium or platinum acetate, palladium dibenzylidine acetone, palladium acetylacetonate, and tetrakistriphenylphosphino palladium.

In still another embodiment the phosporous ligand may be any of the mono phosphines, preferably phosphites such as triphenyl phosphine, tris paratolyl phosphine, tris para chlorophenyl phosphine, tris para methoxyphenyl phosphine, tricyclohexyl phosphine, tributyl phosphine, and methyl diphenyl phosphine.

In another embodiment the number of moles of the anionic semilabile ligand per gram atom of metal, may be 1 to 10, preferably 1–2.

In still another embodiment the number of moles of protonic acid per gram atom of metal, may be 1 to 10, preferably 2 to 3.

In yet another embodiment the ratio of number of moles of the mono phosphine ligand per gram of metal, may be 1 to 10 preferably 2 to 3.

The invention also provides a process for preparation of said metal complexes, which comprises the steps of reacting a group VIII metal source with a semilabile anionic chelating ligand which contains a N donor and an $O^-$ group, a monodentate phosphorus ligand and the corresponding protonic acid in an organic solvent, under constant stirring at ambient temperature for a period ranging from 1 to 15 minutes, precipitating the product using a suitable organic solvent, washing and drying the precipitate to obtain the product.

In one of the embodiments, the preparation of group VIII metal complexes having general formula 1 where X=halides may also be carried out by mixing any of the corresponding halide salts with a solution of compound having formula 1 wherein X is an aryl or alkyl sulphonato or formato group, in an organic solvent, under constant stirring at ambient temperature for a period ranging from 1 to 15 minutes, filtering, washing and drying the precipitate to obtain the product.

In another embodiment, the protonic acid may be selected from, para toluene sulphonic acid, methane sulphonic acid, trifluoro methane sulphonic acid, acetic acid, formic acid, oxalic acid and trifluoro acetic acid.

In yet another embodiment the halide salts may be such as lithium chloride, lithium bromide, lithium iodide, sodium chloride, sodium bromide, sodium iodide, potassium chloride, potassium bromide, or potassium iodide.

In still another embodiment the solvent may be such as chloroform, dichloromethane, aromatic hydrocarbons, like, benzene, toluene, xylenes, ketones, like methyl ethyl ketone, acetone, amides like N-methyl pyrrolidone, or alcohols like, methanol, ethanol.

The process of the present invention is described herein below with reference to examples, which are illustrative only and should not be construed to limit the scope of the present invention in any manner.

EXAMPLE 1

Pd(OAc)$_2$: 0.89 mmol, 2-picolinic acid: 0.89 mmol, triphenyl phosphine: 1.8 mmol and para toluene sulphonic acid: 1.8 mmol were dissolved in chloroform at room temperature and shaken vigorously for 2 minutes, by instantaneous formation the solution turns a deep yellow color. The product was then precipitated out as a yellow oil using diethyl ether, which was washed several times with diethyl ether and n-hexane. This oil, on vacuum drying, gave stable yellow porous crystals with yield=99%.

EXAMPLE 2

Pt(OAc)$_2$: 0.89 mmol, 2-picolinic acid: 0.89 mmol, triphenyl phosphine: 1.8 mmol and para toluene sulphonic acid: 1.8 mmol were dissolved in chloroform at room temperature and shaken vigorously for 2 minutes, by instantaneous formation the solution turns a deep yellow color. The product was then precipitated out as an yellow oil using diethyl ether, which was washed several times with diethyl ether and n-hexane. This oil, on vacuum drying, gave stable yellow porous crystals with yield=99%.

EXAMPLE 3

Pd(OAc)$_2$: 0.89 mmol, 2-pipecolinic acid: 0.89 mmol, triphenyl phosphine: 1.8 mmol and para toluene sulphonic acid: 1.8 mmol were dissolved in chloroform at room temperature and stirred well for 5 minutes, immediately forming a deep yellow solution. The product was then precipitated out as an yellow oil using diethyl ether, which was washed several times with diethyl ether and n-hexane. This oily product, on vacuum drying, gave stable yellow porous crystals with yield=98%.

EXAMPLE 4

Pd(OAc)$_2$: 0.89 mmol, 8-hydroxy quinoline: 0.89 mmol, triphenyl phosphine: 1.8 mmol and para toluene sulphonic acid: 1.8 mmol were dissolved in chloroform at room temperature and stirred well for 5 minutes, immediately forming a deep yellow solution. The product was then precipitated out as an yellow oil using diethyl ether, which was washed several times with diethyl ether and n-hexane. This oily product on vacuum drying gave stable yellow porous crystals with yield=98%.

EXAMPLE 5

Pd(OAc)$_2$: 0.89 mmol, 2-picolinic acid: 0.89 mmol, tris para chloro phenyl phosphine: 1.8 mmol and para toluene sulphonic acid: 1.8 mmol were dissolved in chloroform at room temperature and stirred well for 15 min. resulting in a deep yellow solution. The product was then precipitated out as a yellow solid, using diethyl ether, which was washed several times with diethyl ether and n-hexane and vacuum dried. Yield was 98%.

EXAMPLE 6

Pd(OAc)$_2$: 0.89 mmol, 2-picolinic acid: 0.89 mmol, tris para tolyl phosphine: 1.8 mmol and para toluene sulphonic acid: 1.8 mmol were dissolved in chloroform at room temperature and stirred well for 5 min, resulting in a deep yellow solution. The product was then precipitated out as a yellow oil using diethyl ether, which was washed several times with diethyl ether and n-hexane. This oil, on vacuum drying, gave stable yellow porous crystals with 98% yield.

EXAMPLE 7

Pd(OAc)$_2$: 0.89 mmol, 2-picolinic acid: 0.89 mmol, triphenyl phosphine: 1.8 mmol and methane sulphonic acid: 1.8 mmol were dissolved in chloroform at room temperature and shaken thoroughly for 2 minutes, immediately forming a deep yellow solution. The product was then precipitated out as an yellow oil using diethyl ether, which was washed several times with diethyl ether and n-hexane. This oil, on vacuum drying, gave stable yellow porous crystals with 98% yield.

EXAMPLE 8

Pd(OAc)$_2$: 0.89 mmol, 2-picolinic acid: 0.89 mmol, tri-cyclohexyl phosphine: 1.8 mmol and para toluene sulphonic acid: 1.8 mmol were dissolved in chloroform at room temperature and stirred well for 15 min, resulting in a deep yellow solution. The product was then precipitated out as a yellow oil using diethyl ether, which was washed several times with diethyl ether and n-hexane. This oil, on vacuum drying, gave stable yellow porous crystals with 95% yield.

EXAMPLE 9

Pd(OAC)$_2$: 0.89 mmol, 2-picolinic acid: 0.89 mmol, triphenyl phosphine: 1.8 mmol and formic acid: 1.8 mmol were dissolved in chloroform at room temperature and stirred well for 15 min. resulting in a deep yellow solution. The product was then precipitated out as a yellow oil using diethyl ether, which was washed several times with diethyl ether and n-hexane. This oil, on vacuum drying, gave stable yellow porous crystals with yield=95%.

EXAMPLE 10

The complex obtained from example 1: 0.89 mmol, lithium chloride: 0.89 mmol were dissolved in chloroform at room temperature and stirred well for 15 min. forming a pale yellow precipitate. This precipitate was filtered, washed several times with diethyl ether and n-hexane and dried under vacuum. Yield +93.%.

Advantages of Present Invention

1. Invention of new transition metal complexes which are stable and may be useful catalysts for a variety of carbonylation and co-polymerization reactions.

2. An easy single step process for the synthesis of a series of transition metal complexes with high yield.

We claim:

1. Novel group VIII transition metal complex represented by the general formula shown herein below:

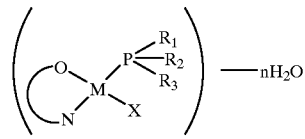

Formula 1 wherein M is group VIII transition metal; N⌒O⁻ represents a semilabile anionic chelating ligand; $R_1$, $R_2$ & $R_3$ are substituents on phosphine ligand selected from the group consisting of hydrogen, alkyl, arylalkyl, and cycloaliphatic groups, X is a sulphonato, carboxylato, formato group or halide selected from Cl⁻, Br⁻ or I⁻ and 1<n<10.

2. The novel metal complex claimed in claim 1, wherein the semilabile anionic chelating ligand is an organic compound, containing an N donor and an O group.

3. The metal complex as claimed in claim 1, wherein the anionic chelating ligand is selected from the group of organic compounds consisting of 8-hydroxyl quinoline, 2-hydroxy pyridine, 2-(2-hydroxy ethyl)pyridine, pyridyl-2-carboxylate, piperidyl-2-carboxylate, quinolyl-2-carboxylate, isoquinolyl-1-carboxylate and isoquinolyl-3-carboxylate, pyridyl-2-carboxylate, piperidyl-2-carboxylate, and 8-hydroxyquinoline.

4. The metal complex as claimed in claim 1, wherein the metal is selected from the group consisting of palladium and platinum.

5. The metal complex as claimed in claim 4, wherein the source of the palladium or platinum is selected from the group consisting of platinum acetate, palladium dibenzylidine acetone, palladium acetylacetonate, and tetrakistriphenylphosphino palladium.

6. The metal complex as claimed in claim 1, wherein the phosphorous ligand is a mono phosphine selected from the group consisting of triphenyl phosphine, tris paratolyl phosphine, tris para chlorophenyl phosphine, tris para methoxyphenyl phosphine, tricyclohexyl phosphine, tributyl phosphine and methyl diphenyl phosphine.

7. The metal complex as claimed in claim 1, wherein the number of moles of the anionic semilabile ligand per gram atom of metal is 1 to 10.

8. The metal complex as claimed in claim 1, wherein the number of moles of protonic acid per gram atom of metal is 1 to 10.

9. The metal complex as claimed in claim 1, wherein the number of moles of protonic acid per gram atom of metal is 2–3.

10. A process for the preparation of group VIII metal complexes of claim 1 comprising reacting a group VIII metal source with a semilabile anionic chelating ligand which contains a N donor and an O⁻ group, a monodentate phosphorus ligand and a protonic acid in an organic solvent, under constant stirring at ambient temperature for a period ranging from 1 to 15 minutes precipitating the product using a suitable organic solvent, washing and drying the precipitate to obtain the product.

11. A process as claimed in claim 10 wherein the preparation of group VIII metal complexes where X=halides is optionally carried out by mixing any of the corresponding halide salts with a solution of compound having formula 1 wherein X is a aryl or alkyl sulphonato or aryl or alkyl carboxylato formato group as halides, in an organic solvent, under constant stirring at ambient temperature for a period ranging from 1 to 15 minutes, filtering, washing and drying the precipitate to obtain the product.

12. The process as claimed in claim 10, wherein the protonic acid is selected from the group consisting of para toluene sulphonic acid, methane sulphonic acid, trifluoro methane sulphonic acid, acetic acid, formic acid, oxalic acid and trifluoro acetic acid.

13. The process as claimed in claim 10, wherein the halide salts are selected from the group consisting of lithium chloride, lithium bromide, lithium iodide, sodium chloride, sodium bromide, sodium iodide, potassium chloride, potassium bromide, and potassium iodide.

14. The process as claimed in claim 10, wherein the solvent is selected from the group consisting of chloroform, dichloromethane, aromatic hydrocarbons, benzene, toluene, xylene, ketones, methyl ethyl ketone, amides, methyl pyrrolidine, alcohols, methanol and ethanol.

15. The metal complex as claimed in claim 7, wherein the number of moles of the anionic semilabile ligand per gram atom of metal is 1–2.

* * * * *